United States Patent [19]

Englert et al.

[11] Patent Number: 5,607,976
[45] Date of Patent: Mar. 4, 1997

[54] SUBSTITUTED BENZENESULFONYL-THIOUREAS AND PHARMACEUTICAL PREPARATIONS CONTAINING THEM

[75] Inventors: Heinrich Englert, Hofheim; Uwe Gerlach, Hattersheim; Peter Crause, Offenbach; Dieter Mania, Königstein; Heinz Gögelein; Joachim Kaiser, both of Frankfurt, all of Germany

[73] Assignee: Hoechst Aktiengesellschaft, Frankfurt am Main, Germany

[21] Appl. No.: 598,319

[22] Filed: Feb. 8, 1996

[30] Foreign Application Priority Data

Feb. 10, 1995 [DE] Germany ............ 195 04 379.0

[51] Int. Cl.$^6$ .................... A61K 31/18; C07C 311/58
[52] U.S. Cl. .................... 514/584; 514/365; 514/593; 546/332; 548/204; 548/561; 549/77; 549/498; 564/23; 564/40
[58] Field of Search .................... 564/23, 40; 514/584

[56] References Cited

U.S. PATENT DOCUMENTS

| | | |
|---|---|---|
| 3,494,936 | 2/1970 | Weyer et al. . |
| 3,917,690 | 11/1975 | Weber et al. . |
| 3,998,968 | 12/1976 | Hitzel et al. . |
| 5,215,985 | 6/1993 | Murphy et al. . |

FOREIGN PATENT DOCUMENTS

| | | |
|---|---|---|
| 754454 | 2/1971 | Belgium . |
| 612724A1 | 8/1994 | European Pat. Off. . |
| 1518874 | 5/1970 | Germany . |
| 2413514 | 2/1976 | Germany . |
| 3011153 | 10/1981 | Germany . |
| 0243821 | 3/1987 | Germany . |
| 1122820 | 8/1968 | United Kingdom . |
| 1212695 | 11/1970 | United Kingdom . |
| 1272354 | 4/1972 | United Kingdom . |

OTHER PUBLICATIONS

W. Linz et al., Cardiovascular Effects of the Novel Potassium Channel Opener (3S, 4R)-3-Hydroxy-2, 2-dimethyl-4-(2-oxo-1-pyrrolidinyl)-6-phenylsulfonylchromane Hemihydrate, Arzneimittel-Forschung/Drug Research, 42 (II), 10, 1180–1185 (1992).

*Primary Examiner*—Robert W. Ramsuer
*Attorney, Agent, or Firm*—Finnegan, Henderson, Farabow, Garrett & Dunner, L.L.P.

[57] ABSTRACT

Substituted benzenesulfonylureas and -thioureas, processes for their preparation, their use for the production of pharmaceutical preparations, and pharmaceutical preparations containing them.

Substituted benzenesulfonylureas and -thioureas of the formula I

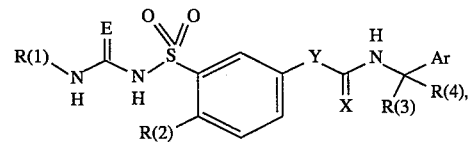

exhibit effects on the cardiovascular system.

8 Claims, No Drawings

SUBSTITUTED BENZENESULFONYL-THIOUREAS AND PHARMACEUTICAL PREPARATIONS CONTAINING THEM

DESCRIPTION

This invention relates to substituted benzenesulfonylureas and -thioureas, processes for their preparation, their use for the production of pharmaceutical preparations, and pharmaceutical preparations containing them.

The invention relates to substituted benzenesulfonylureas and -thioureas of the formula I

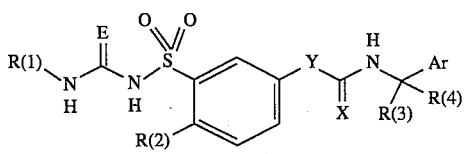

in which:

R(1) is hydrogen, alkyl having 1, 2, 3, 4, 5 or 6 carbon atoms or cycloalkyl having 3, 4, 5 or 6 carbon atoms;

R(2) is alkyl having 1, 2, 3, 4, 5 or 6 carbon atoms, alkoxy having 1, 2, 3, 4, 5 or 6 carbon atoms, mercaptoalkyl having 1, 2, 3, 4, 5 or 6 carbon atoms, cycloalkyl having 3, 4, 5 or 6 carbon atoms or ($C_1$–$C_8$) chains in which one to three carbon atoms can be replaced by heteroatoms selected from the group consisting of O, NH and S;

R(3) and R(4) are identical or different and are hydrogen, alkyl having 1, 2, 3, 4, 5 or 6 carbon atoms, or together form a $(CH_2)_{2-5}$ chain;

E is oxygen or sulfur;

X is oxygen or sulfur;

Y is a hydrocarbon chain of the formula $[CR(5)_2]_m$;
R (5) is hydrogen or alkyl having 1 or 2 carbon atoms;
m is 1 or 2;

Ar is phenyl, thienyl, furyl, pyrrolyl, thiazolyl, naphthyl, or pyridyl, which in each case is unsubstituted or substituted by one to 3 substituents selected from the group consisting of alkyl having 1 or 2 carbon atoms, alkoxy having 1 or 2 carbon atoms, Cl, Br and F.

Regarding replacement of carbon atoms with O, NH, or S in R(2), in one embodiment replacement of a carbon atom other than the carbon atom adjacent to the phenyl moiety may occur.

The term alkyl describes, if not stated otherwise, straight-chain or branched saturated hydrocarbon radicals. The cycloalkyl radical can additionally carry an alkyl substituent. Halogen substituents which can be employed are the elements fluorine, chlorine, bromine and iodine. Furthermore, compounds having centers of chirality, for example in the alkyl chains Y, R(2), R(3) and R(4), can occur. In this case, the invention includes both the individual antipodes per se, and a mixture of the two enantiomers in different proportions, and also the associated meso compounds or mixtures of meso compounds, the enantiomers or diastereomers.

Similar sulfonylureas having hypoglycemic action are disclosed in Belgian Patent 754 454.

The compounds I are used as pharmaceutical active compounds in human and veterinary medicine. They can further be used as intermediates for the production of further pharmaceutical active compounds.

Preferred compounds I are those in which:

R(1) is hydrogen, alkyl having 1, 2, 3, 4, 5 or 6 carbon atoms or cycloalkyl having 3, 4, 5 or 6 carbon atoms;

R(2) is alkyl having 1, 2, 3, 4, 5 or 6 carbon atoms, alkoxy having 1, 2, 3, 4, 5 or 6 carbon atoms, mercaptoalkyl having 1, 2, 3, 4, 5 or 6 carbon atoms, cycloalkyl having 3, 4, 5 or 6 carbon atoms or ($C_1$–$C_8$) chains in which 1 to 3 carbon atoms can be replaced by heteroatoms selected from the group consisting of O, NH and S;

R(3) and R(4) are identical or different and are hydrogen, alkyl having 1, 2, 3, 4, 5 or 6 carbon atoms or together form a $(CH_2)_{2-5}$ chain;

E is sulfur;

X is oxygen;

Y is a hydrocarbon chain of the formula $[CR(5)_2]_{1-2}$,
R(5) is hydrogen or alkyl having 1 or 2 carbon atoms;

Ar is phenyl, thienyl, furyl, pyrrolyl, thiazolyl, naphthyl, or pyridyl,
which in each case is unsubstituted or substituted by one to 3 substituents selected from the group consisting of alkyl having 1 or 2 carbon atoms, alkoxy having 1 or 2 carbon atoms, Cl, Br and F unsubstituted or substituted Very particularly preferred compounds I are those in which:

R(1) is hydrogen or alkyl having 1 or 2 carbon atoms;

R(2) is alkoxy having 1, 2, 3, 4, 5 or 6 carbon atoms;

R(3) and R(4) are identical or different and are hydrogen, alkyl having 1, 2, 3, 4, 5 or 6 carbon atoms;

E is sulfur;

X is oxygen;

Y is a hydrocarbon chain of the formula $(CH_2)_{1-2}$;

Ar is phenyl, thienyl, furyl, pyrrolyl, thiazolyl, naphthyl, or pyridyl,
which in each case is unsubstituted or substituted by one to 3 substituents selected from the group consisting of alkyl having 1 or 2 carbon atoms, alkoxy having 1 or 2 carbon atoms, Cl, Br and F.

In addition, the compounds I form a preferred group in which:

R(1) is hydrogen or alkyl having 1 or 2 carbon atoms;

R(2) is alkoxy having 1, 2, 3, 4, 5 or 6 carbon atoms;

R(3) and R(4) are identical or different and are hydrogen or methyl;

E is sulfur;

X is oxygen;

Y is a hydrocarbon chain of the formula $(CH_2)_{1-2}$;

Ar is thienyl, furyl, pyrrolyl, thiazolyl, naphthyl, or pyridyl,
which in each case is unsubstituted or substituted by one to 3 substituents selected from the group consisting of alkyl having 1 or 2 carbon atoms, alkoxy having 1 or 2 carbon atoms, Cl, Br and F.

Likewise preferred compounds of the formula I are those in which:

R(1) is hydrogen or alkyl having 1 or 2 carbon atoms;

R(2) is alkoxy having 1, 2, 3, 4, 5 or 6 carbon atoms;

R(3) and R(4) are identical or different and are hydrogen or methyl;

E is sulfur;

X is oxygen;

Y is a hydrocarbon chain of the formula $(CH_2)_{1-2}$;

Ar is phenyl, which is unsubstituted or substituted by one to 3 substituents selected from the group consisting of alkyl having 1 or 2 carbon atoms, alkoxy having 1 or 2 carbon atoms, Cl, Br and F.

The compounds of the present invention are useful pharmaceuticals for the treatment of cardiac arrhythmias of all types of origin and for the prevention of sudden heart death due to arrhythmia and can therefore be used as antiarrhythmics. Examples of arrhythmic disorders of the heart are supraventricular arrhythmias such as atrial tachycardias, atrial flutters or paroxysmal supraventricular arrhythmias or ventricular arrhythmias such as ventricular extrasystoles, but in particular life-threatening ventricular tachycardias or the particularly dangerous ventricular fibrillation. They are suitable, in particular, for those cases where arrhythmias are the consequence of a constriction of a coronary vessel, such as occur in angina pectoris or during an acute cardiac infarct or as a chronic consequence of a cardiac infarct. They are therefore particularly suitable in postinfarct patients for the prevention of sudden heart death. Further syndromes where arrhythmias of this type and/or sudden heart death due to arrhythmia play a part are, for example, cardiac insufficiency or cardiac hypertrophy as a consequence of a chronically increased blood pressure. Moreover, the compounds can positively affect a decreased contractility of the heart. This can include a disease-related fall in cardiac contractility, such as in cardiac insufficiency, but also acute cases such as heart failure in the case of the effects of shock. Likewise, in the case of a heart transplantation, after operation has taken place the heart can resume its operational capacity more rapidly and reliably. The same applies to operations on the heart, which necessitate a temporary stopping of cardiac activity by means of cardioplegic solutions.

The invention furthermore relates to a process for the preparation of the compounds I, which comprises (a) reacting aromatic sulfonamides of the formula II

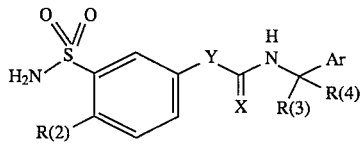

or their salts of the formula III

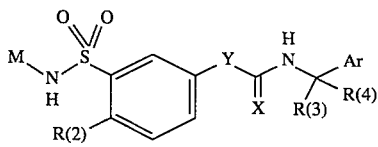

with R(1)-substituted isocyanates of the formula IV

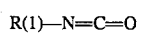

to give substituted benzenesulfonylureas I a (E=oxygen)

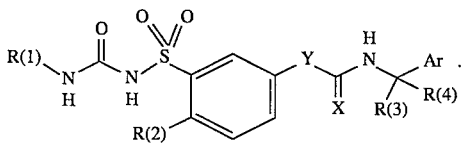

Suitable cations M in the salts of the formula III are alkali metal, alkaline earth metal, ammonium and tetraalkylammonium ions. Equivalently to the R(1)-substituted isocyanates IV, R(1)-substituted carbamic acid esters, R(1)-substituted carbamoyl halides or R(1)-substituted ureas can be employed.

(b) Unsubstituted benzenesulfonylureas I a [R(1)=H, E=O] can be prepared by reaction of an aromatic benzenesulfonamide of the formula II or of its salt III with trialkylsilyl isocyanate or silicon tetraisocyanate and cleavage (e.g. hydrolysis) of the primary silicon-substituted benzenesulfonylureas.

It is furthermore possible to convert a benzenesulfonamide II or its salt III into a benzenesulfonylurea I a by reaction with cyanogen halides and hydrolysis of the primarily formed N-cyanosulfonamides with mineral acids at temperatures from 0° C. to 100° C.

(c) A benzenesulfonylurea I a (where E=oxygen) can be prepared from an aromatic benzenesulfonamide II or its salt III using an R(1)-substituted trichloroacetamide of the formula V

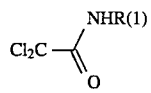

in the presence of a base in an inert solvent according to Synthesis 1987, 734–735 at temperatures from 25° C. to 150° C.

Suitable bases are, for example, alkali metal or alkaline earth metal hydroxides, hydrides, amides or alternatively alkoxides, such as sodium hydroxide, potassium hydroxide, calcium hydroxide, sodium hydride, potassium hydride, calcium hydride, sodium amide, potassium amide, sodium methoxide, sodium ethoxide, potassium methoxide or potassium ethoxide. Suitable inert solvents are ethers such as tetrahydrofuran, dioxane, ethylene glycol dimethyl ether (diglyme), ketones such as acetone or butanone, nitriles such as acetonitrile, nitro compounds such as nitromethane, esters such as ethyl acetate, amides such as dimethylformamide (DMF) or N-methylpyrrolidone (NMP), hexamethylphosphoramide, sulfoxides such as DMSO, sulfones such as sulfolane, hydrocarbons such as benzene, toluene, xylenes. Furthermore, mixtures of these solvents with one another are also suitable.

(d) A benzenesulfonylthiourea I b (E=S)

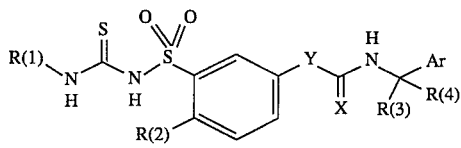

is prepared from a benzenesulfonamide II or its salt III and an R(1)-substituted isothiocyanate VI

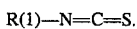

An unsubstituted benzenesulfonylthiourea I b [R(1)=H, X=S] can be prepared by reaction of an aromatic benzenesulfonamide II or its salt III with trimethylsilyl isothiocyanate or silicon tetraisothiocyanate and cleavage (hydrolysis) of the primarily formed silicon-substituted benzenesulfonylurea. Furthermore, it is possible to react an aromatic benzenesulfonamide II or its salt III with benzoyl isothiocyanate and to react the intermediate benzoyl-substituted benzenesulfonylthiourea with an aqueous mineral acid to give I b [R(1)=H, E=S]. Similar processes are described in J. Med. Chem. 1992, 35, 1137–1144. A further variant consists in reacting the N-cyanosulfonamides mentioned under process 1 with hydrogen sulfide.

(e) A substituted benzenesulfonylurea of the formula I a (E=oxygen) can be prepared by a conversion reaction of a benzenesulfonylthiourea of the structure I b (E=S).

The replacement of the sulfur atom by an oxygen atom in the appropriately substituted benzenesulfonylthiourea can be carried out, for example, with the aid of oxides or salts of heavy metals or also by use of oxidants such as hydrogen peroxide, sodium peroxide or nitrous acid. A thiourea can also be desulfurized by treatment with phosgene or phosphorus pentachloride. The intermediate compounds obtained are chloroformamidines or carbodiimides, which are converted into the corresponding substituted benzenesulfonylureas, for example, by hydrolysis or addition of water. During desulfurization, isothioureas behave like thioureas and can accordingly also be used as starting substances for these reactions.

(f) A benzenesulfonylurea I a can be prepared from a benzenesulfonyl halide of the formula VII

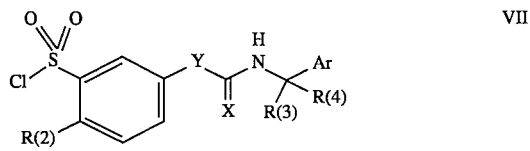

using an R(1)-substituted urea or an R(1)-substituted bis-(trialkylsilyl)urea. Furthermore, the sulfonyl chloride VII can be reacted with parabanic acid to give a benzenesulfonylparabanic acid whose hydrolysis with mineral acids yields the corresponding benzenesulfonylurea I a.

(g) A benzenesulfonylurea I a can be prepared by reaction of an amine of the formula R(1)—NH$_2$ with a benzenesulfonyl isocyanate of the formula VIII

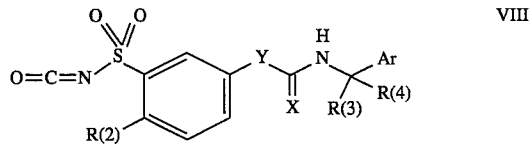

Likewise, an amine R(1)—NH$_2$ can be reacted with a benzenesulfonylcarbamic acid ester, a carbamoyl halide or a benzenesulfonylurea I a [where R(1)=H] to give the compounds I.

(h) A benzenesulfonylthiourea I b can be prepared by reaction of an amine of the formula R(1)—NH$_2$ with a benzenesulfonyl isothiocyanate of the formula IX

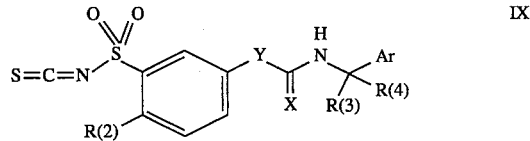

Likewise, an amine R(1)—NH$_2$ can be reacted with a benzenesulfonylcarbamic acid thioester or a thiocarbamoyl halide to give the compounds Ib. The sulfonyl isothiocyanates were prepared by reaction of a corresponding sulfonamide with equimolar amounts of alkali metal hydroxide and carbon disulfide in an organic solvent, such as DMF, DMSO or N-methylpyrrolidone. The di-alkali metal salt of the sulfonyldithiocarbamic acid obtained is reacted in an inert solvent with a slight excess of phosgene, or substitute of the same, such as triphosgene, a chloroformic acid ester (2 equivalents) or thionyl chloride. The solution of the sulfonyl isothiocyanate obtained can be reacted directly with the corresponding amines or ammonia.

(i) An appropriately substituted benzenesulfenyl- or -sulfinylurea can be oxidized to give the benzenesulfonylurea I a using an oxidant, such as hydrogen peroxide, sodium peroxide or nitrous acid.

The compounds I and their physiologically acceptable salts are useful therapeutics which are suitable not only as antiarrhythmics, but as prophylaxis in disorders of the cardiovascular system, cardiac insufficiency, heart transplantation or cerebral vascular disorders in humans or mammals (for example monkeys, dogs, mice, rats, rabbits, guinea-pigs and cats). Physiologically acceptable salts of the compounds I are understood according to Remmington's Pharmaceutical Science, 17th edition, 1985, pages 14–18 as meaning compounds of the formula XII which can be prepared from nontoxic organic and inorganic bases and substituted benzenesulfonylureas I. Salts are

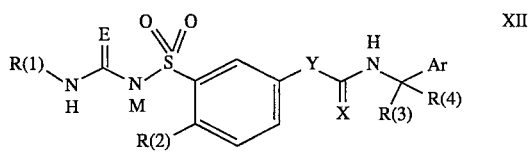

preferred in this context in which M in the formula XII is a sodium, potassium, rubidium, calcium, magnesium or ammonium ion, and can also be the acid addition products of basic amino acids, such as lysine or arginine.

The starting compounds for the mentioned synthesis processes of the benzenesulfonylureas I are prepared by methods known per se, as are described in the literature (for example in the standard works such as Houben-Weyl, Methoden der Organischen Chemie (Methods of Organic Chemistry), Georg Thieme Verlag, Stuttgart; Organic Reactions, John Wiley & Sons, Inc., New York; and also in the patent applications indicated above), namely under reaction conditions which are known and suitable for the reactions mentioned. In this case, use can also be made of variants which are known per se but not mentioned here in more detail. If desired, the starting substances can also be formed in situ in such a way that they are not isolated from the reaction mixture, but immediately reacted further.

The starting compounds for the mentioned synthesis processes of the benzenesulfonyl(thio)ureas I are prepared by methods known per se, as are described in the literature (for example in the standard works such as Houben-Weyl, Methoden der Organischen Chemie (Methods of Organic Chemistry), Georg Thieme Verlag, Stuttgart; Organic Reactions, John Wiley & Sons, Inc., New York; and also in the patent applications indicated above), namely under reaction conditions which are known and suitable for the reactions mentioned. In this case, use can also be made of variants which are known per se but not mentioned here in more detail. If desired, the starting substances can also be formed in situ in such a way that they are not isolated from the reaction mixture, but immediately reacted further.

Suitably substituted carboxylic acids of the formula XIII

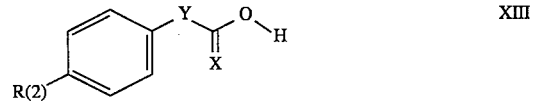

can thus be subjected to a halosulfonation and the sulfonamide XIV

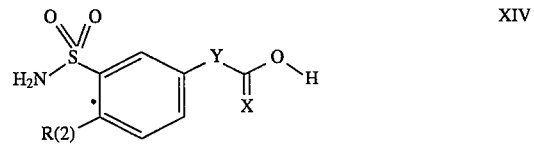

obtained by subsequent ammonolysis can be reacted with an appropriate amine R(3)R(4)NH after activation of the carboxylic acid group to give the carboxamide of the formula

II

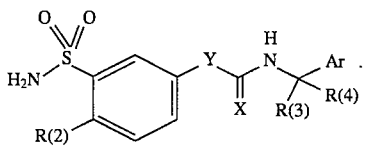

II

Suitable activation methods are the preparation of the carbonyl chloride or of the ester or mixed carboxylic anhydrides using formyl halides. In addition, the reagents known for amide bond preparation such as carbonyldiimidazole, dicyclohexylcarbodiimide and propanephosphoric anhydride can be used.

The sulfonamides XIV are prepared by known methods, namely under reaction conditions which are known and suitable for the reactions mentioned. In this case, use can also be made of variants which are known but not mentioned here in more detail. If desired, the syntheses can be carried out in one, two or more steps. In particular, processes are preferred in which the acid XIII is converted into aromatic sulfonic acids and their derivatives, such as sulfonyl halides, by electrophilic reagents in the presence or absence of inert solvents at temperatures from −10° C. to 120° C., preferably from 0° C. to 100° C. For example, sulfonations can be carried out using sulfuric acids or oleum, halosulfonations using halosulfonic acids, reactions with sulfuryl halides in the presence of anhydrous metal halides or with thionyl halides in the presence of anhydrous metal halides with subsequent oxidations, which are carried out in a known manner, to give aromatic sulfonyl chlorides. If sulfonic acids are the primary reaction products, these can be converted into sulfonyl halides in a known manner by acid halides, such as phosphorus trihalides, phosphorus pentahalides, phosphorus oxychloride, thionyl halides or oxalyl halides, either directly or by treatment with tertiary amines, such as pyridine or trialkylamines, or with alkali metal or alkaline earth metal hydroxides or reagents which form these basic compounds in situ. The sulfonic acid derivatives are converted into sulfonamides in a manner known from the literature, preferably sulfonyl chlorides are reacted in inert solvents with aqueous ammonia in acetone or THF at temperatures from 0° C. to 100° C. Furthermore, aromatic sulfonamides XIV can be synthesized according to processes described in the literature from the acids XIII or their esters by reactions with organic reagents of alkali metals or alkaline earth metals in inert solvents and under an inert gas atmosphere at temperatures from −100° C. to 50° C., preferably from −100° C. to 30° C., with sulfur dioxide and subsequent thermal treatment with an NH$_2$ donor, such as sulfamic acid.

The compounds I according to the invention and their physiologically acceptable salts can be used for the production of pharmaceutical preparations, in particular by a nonchemical route. In this context, they can be brought into a suitable dose form together with at least one solid or liquid excipient or auxiliary on their own or in combination with other pharmaceuticals having cardiovascular activity, such as calcium antagonists, NO donors or ACE inhibitors. These preparations can be used as pharmaceuticals in human or veterinary medicine. Possible excipients are organic or inorganic substances which are suitable for enteral (for example oral) or parenteral administration, for example intravenous administration, or topical applications and do not react with the novel compounds, for example water, vegetable oils, benzyl alcohols, polyethylene glycols, glycerol triacetate, gelatin, carbohydrates such as lactose or starch, magnesium stearate, talc, lanolin and petroleum jelly. In particular, tablets, coated tablets, capsules, syrups, juices or drops are used for oral administration, solutions, preferably oily or aqueous solutions, and also suspensions, emulsions or implants, are used for rectal administration, and creams, pastes, lotions, gels, sprays, foams, aerosols, solutions (for example in alcohols such as ethanol or isopropanol, acetonitrile, DMF, dimethylacetamide, 1,2-propanediol or their mixtures with one another or with water) or powders are used for topical application. The novel compounds can also be lyophilized and the lyophilizates obtained used, for example, for the production of injection preparations. In particular for topical application, liposomal preparations are also suitable. They contain stabilizers and/or wetting agents, emulsifiers, salts and/or auxiliaries such as lubricants, preservatives, salts for affecting the osmotic pressure, buffer substances, colorants and flavorings and/or aromatic substances. If desired, they can also contain one or more further active compounds, for example one or more vitamins.

The doses which are necessary for the treatment of cardiac arrhythmias with the compounds I depend on whether the therapy is acute or prophylactic. Normally, a dose range of approximately at least 0.1 mg, preferably at least 1 mg, up to at most 100 mg, preferably up to at most 10 mg, per kg per day is adequate if prophylaxis is conducted. The dose can in this case be divided as an oral or parenteral individual dose or else in up to four individual doses. If acute cases of cardiac arrhythmias are treated, for example in an intensive care unit, parenteral administration can be advantageous. A preferred dose range in critical situations can then be 10 to 100 mg and be administered, for example, as an intravenous continuous infusion.

According to the invention, in addition to the compounds described in the working examples, the compounds I compiled in the following Table can be obtained:

1) N-5-(1-Phenylethyl)aminocarbonylmethyl-2-propoxyphenylsulfonyl-N'-methylthiourea
2) N-5-(1-(2-Furyl)ethyl)aminocarbonylmethyl-2-methoxyphenylsulfonyl-N'-methylthiourea
3) N-5-(1-(3-Furyl)ethyl)aminocarbonylmethyl-2-methoxyphenylsulfonyl-N'-methylthiourea
4) N-5-(1-(2-Thienyl)ethyl)aminocarbonylmethyl-2-methoxyphenylsulfonyl-N'-methylthiourea
5) N-5-(1-(3-Thienyl)ethyl)aminocarbonylmethyl-2-methoxyphenylsulfonyl-N'-methylthiourea
6) N-5-(1-(2-Pyrrolyl)ethyl)aminocarbonylmethyl-2-methoxyphenylsulfonyl-N'-methylthiourea
7) N-5-(1-(3-Pyrrolyl)ethyl)aminocarbonylmethyl-2-methoxyphenylsulfonyl-N'-methylthiourea
8) N-5-(1-(2-Thiazolyl)ethyl)aminocarbonylmethyl-2-methoxyphenylsulfonyl-N'-methylthiourea
9) N-5-(1-(3-Thiazolyl)ethyl)aminocarbonylmethyl-2-methoxyphenylsulfonyl-N'-methylthiourea
10) N-5-(1-(2-Furyl)ethyl)aminocarbonylmethyl-2-methoxyphenylsulfonyl-N'-methylurea
11) N-5-(1-(3-Furyl)ethyl)aminocarbonylmethyl-2-methoxyphenylsulfonyl-N'-methylurea
12) N-5-(1-(2-Thienyl)ethyl)aminocarbonylmethyl-2-methoxyphenylsulfonyl-N'-methylurea
13) N-5-(1-(3-Thienyl)ethyl)aminocarbonylmethyl-2-methoxyphenylsulfonyl-N'-methylurea
14) N-5-(1-(2-Pyrrolyl)ethyl)aminocarbonylmethyl-2-methoxyphenylsulfonyl-N'-methylurea
15) N-5-(1-(3-Pyrrolyl)ethyl)aminocarbonylmethyl-2-methoxyphenylsulfonyl-N'-methylurea
16) N-5-(1-(2-Thiazolyl)ethyl)aminocarbonylmethyl-2-methoxyphenylsulfonyl-N'-methylurea
17) N-5-(1-(2-Furyl)ethyl)aminocarbonylmethyl-2-methylphenylsulfonyl-N'-methylthiourea 18) N-5-(1-(3-Furyl)ethyl)aminocarbonylmethyl-2-methylphenylsulfonyl-N'-methylthiourea
19) N-5-(1-(2-Thienyl)ethyl)aminocarbonylmethyl-2-methylphenylsulfonyl-N'-methylthiourea
20) N-5-(1-(3-Thienyl)ethyl)aminocarbonylmethyl-2-methylphenylsulfonyl-N'-methylthiourea
21) N-5-(1-(2-Pyrrolyl)ethyl)aminocarbonylmethyl-2methylphenylsulfonyl-N'-methylthiourea
22) N-5-(1-(3-Pyrrolyl)ethyl)aminocarbonylmethyl-2-methylphenylsulfonyl-N'-methylthiourea
23) N-5-(1-(2-Thiazolyl)ethyl)aminocarbonylmethyl-2methylphenylsulfonyl-N'-methylthiourea
24) N-5-(1-(3-Thiazolyl)ethyl)aminocarbonylmethyl-2-methylphenylsulfonyl-N'-methylthiourea
25) N-5-(1-(2-Furyl)ethyl)aminocarbonylmethyl-2-methylphenylsulfonyl-N'-methylurea
26) N-5-(1-(3-Furyl)ethyl)aminocarbonylmethyl-2-methylphenylsulfonyl-N'-methylurea
27) N-5-(1-(2-Thienyl)ethyl)aminocarbonylmethyl-2-methylphenylsulfonyl-N'-methylurea
28) N-5-(1-(3-Thienyl)ethyl)aminocarbonylmethyl-2-methylphenylsulfonyl-N'-methylurea
29) N-5-(1-(2-Pyrrolyl)ethyl)aminocarbonylmethyl-2-methylphenylsulfonyl-N'-methylurea
30) N-5-(1-(3-Pyrrolyl)ethyl)aminocarbonylmethyl-2-methylphenylsulfonyl-N'-methylurea
31) N-5-(1-(2-Thiazolyl)ethyl)aminocarbonylmethyl-2methylphenylsulfonyl-N'-methylurea
32) N-5-(1-(3-Thiazolyl)ethyl)aminocarbonylmethyl-2methylthiophenylsulfonyl-N'-methylurea
33) N-5-(1-(2-Furyl)ethyl)aminocarbonylmethyl-2-methylthiophenylsulfonyl-N'-methylthiourea
34) N-5-(1-(3-Furyl)ethyl)aminocarbonylmethyl-2-methylthiophenylsulfonyl-N'-methylthiourea
35) N-5-(1-(2-Thienyl)ethyl)aminocarbonylmethyl-2-methylthiophenylsulfonyl-N'-methylthiourea
36) N-5-(1-(3-Thienyl)ethyl)aminocarbonylmethyl-2-methylthiophenylsulfonyl-N'-methylthiourea
37) N-5-(1-(2-Pyrrolyl)ethyl)aminocarbonylmethyl-2-methylthiophenylsulfonyl-N'-methylthiourea
38) N-5-(1-(3-Pyrrolyl)ethyl)aminocarbonylmethyl-2-methylthiophenylsulfonyl-N'-methylthiourea
39) N-5-(1-(2-Thiazolyl)ethyl)aminocarbonylmethyl-2methylthiophenylsulfonyl-N'-methylthiourea
40) N-5-(1-(3-Thiazolyl)ethyl)aminocarbonylmethyl-2methylthiophenylsulfonyl-N'-methylthiourea
41) N-5-(1-(2-Furyl)ethyl)aminocarbonylmethyl-2-methylthiophenylsulfonyl-N'-methylurea
42) N-5-(1-(3-Furyl)ethyl)aminocarbonylmethyl-2-methylthiophenylsulfonyl-N'-methylurea
43) N-5-(1-(2-Thienyl)ethyl)aminocarbonylmethyl-2-methylthiophenylsulfonyl-N'-methylurea
44) N-5-(1-(3-Thienyl)ethyl)aminocarbonylmethyl-2-methylthiophenylsulfonyl-N'-methylurea
45) N-5-(1-(2-Pyrrolyl)ethyl)aminocarbonylmethyl-2-methylthiophenylsulfonyl-N'-methylurea
46) N-5-(1-(3-Pyrrolyl)ethyl)aminocarbonylmethyl-2-methylthiophenylsulfonyl-N'-methylurea
47) N-5-(1-(2-Thiazolyl)ethyl)aminocarbonylmethyl-2-methylthiophenylsulfonyl-N'-methylurea
48) N-5-(1-(2-Furyl)ethyl)aminocarbonylmethyl-2-ethoxyphenylsulfonyl-N'-methylthiourea
49) N-5-(1-(3-Furyl)ethyl)aminocarbonylmethyl-2-ethoxyphenylsufonyl-N'-methylthiourea
50) N-5-(1-(2-Thienyl)ethyl)aminocarbonylmethyl-2-ethoxyphenylsulfonyl-N'-methylthiourea
51) N-5-(1-(3-Thienyl)ethyl)aminocarbonylmethyl-2-ethoxyphenylsulfonyl-N'-methylthiourea
52) N-5-(1-(2-Pyrrolyl)ethyl)aminocarbonylmethyl-2ethoxyphenylsulfonyl-N'-methylthiourea
53) N-5-(1-(3-Pyrrolyl)ethyl)aminocarbonylmethyl-2ethoxyphenylsulfonyl-N'-methylthiourea
54) N-5-(1-(2-Thiazolyl)ethyl)aminocarbonylmethyl-2ethoxyphenylsulfonyl-N'-methylthiourea
55) N-5-(1-(3-Thiazolyl)ethyl)aminocarbonylmethyl-2ethoxyphenylsulfonyl-N'-methylthiourea
56) N-5-(1-(2-Furyl)ethyl)aminocarbonylmethyl-2-ethoxyphenylsulfonyl-N'-methylurea
57) N-5-(1-(3-Furyl)ethyl)aminocarbonylmethyl-2-ethoxyphenylsulfonyl-N'-methylurea
58) N-5-(1-(2-Thienyl)ethyl)aminocarbonylmethyl-2-ethoxyphenylsulfonyl-N'-methylurea
59) N-5-(1-(3-Thienyl)ethyl)aminocarbonylmethyl-2-ethoxyphenylsulfonyl-N'-methylurea
60) N-5-(1-(2-Pyrrolyl)ethyl)aminocarbonylmethyl-2-ethoxyphenylsulfonyl-N'-methylurea
61) N-5-(1-(3-Pyrrolyl)ethyl)aminocarbonylmethyl-2-ethoxyphenylsulfonyl-N'-methylurea
62) N-5-(1-(2-Thiazolyl)ethyl)aminocarbonylmethyl-2-ethoxyphenylsulfonyl-N'-methylurea
63) N-5-(1-(2-Furyl)ethyl)aminocarbonylmethyl-2-propoxy-phenylsulfonyl-N'-methylthiourea
64) N-5-(1-(3-Furyl)ethyl)aminocarbonylmethyl-2-propoxy-phenylsulfonyl-N'-methylthiourea
65) N-5-(1-(2-Thienyl)ethyl)aminocarbonylmethyl-2-propoxyphenylsulfonyl-N'-methylthiourea
66) N-5-(1-(3-Thienyl)ethyl)aminocarbonylmethyl-2-propoxyphenylsulfonyl-N'-methylthiourea
67) N-5-(1-(2-Pyrrolyl)ethyl)aminocarbonylmethyl-2-propoxyphenylsulfonyl-N'-methylthiourea
68) N-5-(1-(3-Pyrrolyl)ethyl)aminocarbonylmethyl-2-propoxyphenylsulfonyl-N'-methylthiourea
69) N-5-(1-(2-Thiazolyl)ethyl)aminocarbonylmethyl-2-propoxyphenylsulfonyl-N'-methylthiourea
70) N-5-(1-(3-Thiazolyl)ethyl)aminocarbonylmethyl-2-propoxyphenylsulfonyl-N'-methylthiourea
71) N-5-(1-(2-Furyl)ethyl)aminocarbonylmethyl-2-propoxyphenylsulfonyl-N'-methylurea
72) N-5-(1-(3-Furyl)ethyl)aminocarbonylmethyl-2-propoxyphenylsulfonyl-N'-methylurea
73) N-5-(1-(2-Thienyl)ethyl)aminocarbonylmethyl-2-propoxyphenylsulfonyl-N'-methylurea
74) N-5-(1-(3-Thienyl)ethyl)aminocarbonylmethyl-2-propoxyphenylsulfonyl-N'-methylurea
75) N-5-(1-(2-Pyrrolyl)ethyl)aminocarbonylmethyl-2-propoxyphenylsulfonyl-N'-methylurea
76) N-5-(1-(3-Pyrrolyl)ethyl)aminocarbonylmethyl-2-propoxyphenylsulfonyl-N'-methylurea
77) N-5-(1-(2-Thiazolyl)ethyl)aminocarbonylmethyl-2-propoxyphenylsulfonyl-N'-methylurea
78) N-5-(1-Phenylpropyl)aminocarbonylmethyl-2-propoxyphenylsulfonyl-N'-methylthiourea
79) N-5-(1-(2-Furyl)propyl)aminocarbonylmethyl-2-methoxyphenylsulfonyl-N'-methylthiourea
80) N-5-(1-(3-Furyl)propyl)aminocarbonylmethyl-2-methoxyphenylsulfonyl-N'-methylthiourea
81) N-5-(1-(2-Thienyl)propyl)aminocarbonylmethyl-2-methoxyphenylsulfonyl-N'-methylthiourea
82) N-5-(1-(3-Thienyl)propyl)aminocarbonylmethyl-2-methoxyphenylsulfonyl-N'-methylthiourea
83) N-5-(1-(2-Pyrrolyl)propyl)aminocarbonylmethyl-2-methoxyphenysulfonyl-N'-methylthiourea
84) N-5-(1-(3-Pyrrolyl)propyl)aminocarbonylmethyl-2-methoxyphenylsulfonyl-N'-methylthiourea
85) N-5-(1-(2-Thiazolyl)propyl)aminocarbonylmethyl-2-methoxyphenylsulfonyl-N'-methylthiourea 86) N-5-(1-(3-Thiazolyl)propyl)aminocarbonylmethyl-2-methoxyphenylsulfonyl-N'-methylthiourea
87) N-5-(1-(2-Furyl)propyl)aminocarbonylmethyl-2-methoxyphenylsulfonyl-N'-methylurea
88) N-5-(1-(3-Furyl)propyl)aminocarbonylmethyl-2-methoxyphenylsulfonyl-N'-methylurea
89) N-5-(1-(2-Thienyl)propyl)aminocarbonylmethyl-2-methoxyphenylsulfonyl-N'-methylurea
90) N-5-(1-(3-Thienyl)propyl)aminocarbonylmethyl-2-methoxyphenylsulfonyl-N'-methylurea
91) N-5-(1-(2-Pyrrolyl)propyl)aminocarbonylmethyl-2-methoxyphenylsulfonyl-N'-methylurea
92) N-5-(1-(3-Pyrrolyl)propyl)aminocarbonylmethyl-2-methoxyphenylsulfonyl-N'-methylurea
93) N-5-(1-(2-Thiazolyl)propyl)aminocarbonylmethyl-2-methoxyphenylsulfonyl-N'-methylurea
94) N-5-(1-(2-Furyl)propyl)aminocarbonylmethyl-2-methylphenylsulfonyl-N'-methylthiourea
95) N-5-(1-(3-Furyl)propyl)aminocarbonylmethyl-2-methylphenylsulfonyl-N'-methylthiourea
96) N-5-(1-(2-Thienyl)propyl)aminocarbonylmethyl-2-methylphenylsulfonyl-N'-methylthiourea
97) N-5-(1-(3-Thienyl)propyl)aminocarbonylmethyl-2-methylphenylsulfonyl-N'-methylthiourea
98) N-5-(1-(2-Pyrrolyl)propyl)aminocarbonylmethyl-2-methylphenylsulfonyl-N'-methylthiourea
99) N-5-(1-(3-Pyrrolyl)propyl)aminocarbonylmethyl-2-methylphenylsulfonyl-N'-methylthiourea
100) N-5-(1-(2-Thiazolyl)propyl)aminocarbonylmethyl-2-methylphenylsulfonyl-N'-methylthiourea
101) N-5-(1-(3-Thiazolyl)propyl)aminocarbonylmethyl-2methylphenylsulfonyl-N'-methylthiourea
102) N-5-(1-(2-Furyl)propyl)aminocarbonylmethyl-2-methylphenylsulfonyl-N'-methylurea
103) N-5-(1-(3-Furyl)propyl)aminocarbonylmethyl-2-methylphenylsulfonyl-N'-methylurea
104) N-5-(1-(2-Thienyl)propyl)aminocarbonylmethyl-2-methylphenylsulfonyl-N'-methylurea
105) N-5-(1-(3-Thienyl)propyl)aminocarbonylmethyl-2-methylphenylsulfonyl-N'-methylurea
106) N-5-(1-(2-Pyrrolyl)propyl)aminocarbonylmethyl-2-methylphenylsulfonyl-N'-methylurea
107) N-5-(1-(3-Pyrrolyl)propyl)aminocarbonylmethyl-2-methylphenylsulfonyl-N'-methylurea
108) N-5-(1-(2-Thiazolyl)propyl)aminocarbonylmethyl-2methylphenylsulfonyl-N'-methylurea
109) N-5-(1-(3-Thiazolyl)propyl)aminocarbonylmethyl-2-methylthiophenylsulfonyl-N'-methylurea
110) N-5-(1-(2-Furyl)propyl)aminocarbonylmethyl-2-methylthiophenylsulfonyl-N'-methylthiourea
111) N-5-(1-(3-Furyl)propyl)aminocarbonylmethyl-2-methylthiophenylsulfonyl-N'-methylthiourea
112) N-5-(1-(2-Thienyl)propyl)aminocarbonylmethyl-2-methylthiophenylsulfonyl-N'-methylthiourea
113) N-5-(1-(3-Thienyl)propyl)aminocarbonylmethyl-2-methylthiophenylsulfonyl-N'-methylthiourea
114) N-5-(1-(2-Pyrrolyl)propyl)aminocarbonylmethyl-2-methylthiophenylsulfonyl-N'-methylthiourea
115) N-5-(1-(3-Pyrrolyl)propyl)aminocarbonylmethyl-2-methylthiophenylsulfonyl-N'-methylthiourea
116) N-5-(1-(2-Thiazolyl)propyl)aminocarbonylmethyl-2-methylthiophenylsulfonyl-N'-methylthiourea
117) N-5-(1-(3-Thiazolyl)propyl)aminocarbonylmethyl-2-methylthiophenylsulfonyl-N'-methylthiourea
118) N-5-(1-(2-Furyl)propyl)aminocarbonylmethyl-2-methylthiophenylsulfonyl-N'-methylurea
119) N-5-(1-(3-Furyl)propyl)aminocarbonylmethyl-2-methylthiophenylsulfonyl-N'-methylurea
120) N-5-(1-(2-Thienyl)propyl)aminocarbonylmethyl-2-methylthiophenylsulfonyl-N'-methylurea
121) N-5-(1-(3-Thienyl)propyl)aminocarbonylmethyl-2-methylthiophenylsulfonyl-N'-methylurea
122) N-5-(1-(2-Pyrrolyl)propyl)aminocarbonylmethyl-2methylthiophenylsulfonyl-N'-methylurea
123) N-5-(1-(3-Pyrrolyl)propyl)aminocarbonylmethyl-2-methylthiophenylsulfonyl-N'-methylurea
124) N-5-(1-(2-Thiazolyl)propyl)aminocarbonylmethyl-2-methylthiophenylsulfonyl-N'-methylurea
125) N-5-(1-(2-Furyl)propyl)aminocarbonylmethyl-2-ethoxyphenylsulfonyl-N'-methylthiourea
126) N-5-(1-(3-Furyl)propyl)aminocarbonylmethyl-2-ethoxyphenylsulfonyl-N'-methylthiourea
127) N-5-(1-(2-Thienyl)propyl)aminocarbonylmethyl-2-ethoxyphenylsulfonyl-N'-methylthiourea
128) N-5-(1-(3-Thienyl)propyl)aminocarbonylmethyl-2-ethoxyphenylsulfonyl-N'-methylthiourea
129) N-5-(1-(2-Pyrrolyl)propyl)aminocarbonylmethyl-2-ethoxyphenylsulfonyl-N'-methylthiourea
130) N-5-(1-(3-Pyrrolyl)propyl)aminocarbonylmethyl-2-ethoxyphenylsulfonyl-N'-methylthiourea
131) N-5-(1-(2-Thiazolyl)propyl)aminocarbonylmethyl-2-ethoxyphenylsulfonyl-N'-methylthiourea
132) N-5-(1-(3-Thiazolyl)propyl)aminocarbonylmethyl-2-ethoxyphenylsulfonyl-N'-methylthiourea
133) N-5-(1-(2-Furyl)propyl)aminocarbonylmethyl-2-ethoxyphenylsulfonyl-N'-methylurea
134) N-5-(1-(3-Furyl)propyl)aminocarbonylmethyl-2-ethoxyphenylsulfonyl-N'-methylurea
135) N-5-(1-(2-Thienyl)propyl)aminocarbonylmethyl-2-ethoxyphenylsulfonyl-N'-methylurea
136) N-5-(1-(3-Thienyl)propyl)aminocarbonylmethyl-2-ethoxyphenylsulfonyl-N'-methylurea
137) N-5-(1-(2-Pyrrolyl)propyl)aminocarbonylmethyl-2-ethoxyphenylsulfonyl-N'-methylurea
138) N-5-(1-(3-Pyrrolyl)propyl)aminocarbonylmethyl-2-ethoxyphenylsulfonyl-N'-methylurea
139) N-5-(1-(2-Thiazolyl)propyl)aminocarbonylmethyl-2-ethoxyphenylsulfonyl-N'-methylurea
140) N-5-(1-(2-Furyl)propyl)aminocarbonylmethyl-2-propoxyphenylsulfonyl-N'-methylthiourea
141) N-5-(1-(3-Furyl)propyl)aminocarbonylmethyl-2-propoxyphenylsulfonyl-N'-methylthiourea
142) N-5-(1-(2-Thienyl)propyl)aminocarbonylmethyl-2-propoxyphenylsulfonyl-N'-methylthiourea
143) N-5-(1-(3-Thienyl)propyl)aminocarbonylmethyl-2-propoxyphenylsulfonyl-N'-methylthiourea
144) N-5-(1-(2-Pyrrolyl)propyl)aminocarbonylmethyl-2-propoxyphenylsulfonyl-N'-methylthiourea
145) N-5-(1-(3-Pyrrolyl)propyl)aminocarbonylmethyl-2-propoxyphenylsulfonyl-N'-methylthiourea
146) N-5-(1-(2-Thiazolyl)propyl)aminocarbonylmethyl-2-propoxyphenylsulfonyl-N'-methylthiourea
147) N-5-(1-(3-Thiazolyl)propyl)aminocarbonylmethyl-2-propoxyphenylsulfonyl-N'-methylthiourea
148) N-5-(1-(2-Furyl)propyl)aminocarbonylmethyl-2-propoxyphenylsulfonyl-N'-methylurea
149) N-5-(1-(3-Furyl)propyl)aminocarbonylmethyl-2-propoxyphenylsulfonyl-N'-methylurea
150) N-5-(1-(2-Thienyl)propyl)aminocarbonylmethyl-2-propoxyphenylsulfonyl-N'-methylurea
151) N-5-(1-(3-Thienyl)propyl)aminocarbonylmethyl-2-propoxyphenylsulfonyl-N'-methylurea
152) N-5-(1-(2-Pyrrolyl)propyl)aminocarbonylmethyl-2-propoxyphenylsulfonyl-N'-methylurea
153) N-5-(1-(3-Pyrrolyl)propyl)aminocarbonylmethyl-2-propoxyphenylsulfonyl-N'-methylurea 154) N-5-(1-(2-Thiazolyl)propyl)aminocarbonylmethyl-2-propoxyphenylsulfonyl-N'-methylurea
155) N-5-(1-Phenyl-1-methylethyl)aminocarbonylmethyl-2-propoxyphenylsulfonyl-N'-methylthiourea
156) N-5-(1-(2-Furyl)-1-methylethyl)aminocarbonylmethyl-2-methoxyphenylsulfonyl-N'-methylthiourea
157) N-5-(1-(3-Furyl)-1-methylethyl)aminocarbonylmethyl-2-methoxyphenylsulfonyl-N'-methylthiourea
158) N-5-(1-(2-Thienyl)-1-methylethyl)aminocarbonylmethyl-2-methoxyphenylsulfonyl-N'-methylthiourea
159) N-5-(1-(3-Thienyl)-1-methylethyl)aminocarbonylmethyl-2-methoxyphenylsulfonyl-N'-methylthiourea
160) N-5-(1-(2-Pyrrolyl)-1-methylethyl)aminocarbonylmethyl-2-methoxyphenylsulfonyl-N'-methylthiourea
161) N-5-(1-(3-Pyrrolyl)-1-methylethyl)aminocarbonylmethyl-2-methoxyphenylsulfonyl-N'-methylthiourea
162) N-5-(1-(2-Thiazolyl)-1-methylethyl)aminocarbonylmethyl-2-methoxyphenylsulfonyl-N'-methylthiourea
163) N-5-(1-(3-Thiazolyl)-1-methylethyl)aminocarbonylmethyl-2-methoxyphenylsulfonyl-N'-methylthiourea
164) N-5-(1-(2-Furyl)-1-methylethyl)aminocarbonylmethyl-2-methoxyphenylsulfonyl-N'-methylurea
165) N-5-(1-(3-Furyl)-1-methylethyl)aminocarbonylmethyl-2-methoxyphenylsulfonyl-N'-methylurea
166) N-5-(1-(2-Thienyl)-1-methylethyl)aminocarbonylmethyl-2-methoxyphenylsulfonyl-N'-methylurea
167) N-5-(1-(3-Thienyl)-1-methylethyl)aminocarbonylmethyl-2-methoxyphenylsulfonyl-N'-methylurea
168) N-5-(1-(2-Pyrrolyl)-1-methylethyl)aminocarbonylmethyl-2-methoxyphenylsulfonyl-N'-methylurea
169) N-5-(1-(3-Pyrrolyl)-1-methylethyl)aminocarbonylmethyl-2-methoxyphenylsulfonyl-N'-methylurea
170) N-5-(1-(2-Thiazolyl)-1-methylethyl)aminocarbonylmethyl-2-methoxyphenylsulfonyl-N'-methylurea
171) N-5-(1-(2-Furyl)-1-methylethyl)aminocarbonylmethyl-2-methylphenylsulfonyl-N'-methylthiourea
172) N-5-(1-(3-Furyl)-1-methylethyl)aminocarbonylmethyl-2-methylphenylsulfonyl-N'-methylthiourea
173) N-5-(1-(2-Thienyl)-1-methylethyl)aminocarbonylmethyl-2-methylphenylsulfonyl-N'-methylthiourea
174) N-5-(1-(3-Thienyl)-1-methylethyl)aminocarbonylmethyl-2-methylphenylsulfonyl-N'-methylthiourea
175) N-5-(1-(2-Pyrrolyl)-1-methylethyl)aminocarbonylmethyl-2-methylphenylsulfonyl-N'-methylthiourea
176) N-5-(1-(3-Pyrrolyl)-1-methylethyl)aminocarbonylmethyl-2-methylphenylsulfonyl-N'-methylthiourea
177) N-5-(1-(2-Thiazolyl)-1-methylethyl)aminocarbonylmethyl-2-methylphenylsulfonyl-N'-methylthiourea
178) N-5-(1-(3-Thiazolyl)-1-methylethyl)aminocarbonylmethyl-2-methylphenylsulfonyl-N'-methylthiourea
179) N-5-(1-(2-Furyl)-1-methylethyl)aminocarbonylmethyl-2-methylphenylsulfonyl-N'-methylurea
180) N-5-(1-(3-Furyl)-1-methylethyl)aminocarbonylmethyl-2-methylphenylsulfonyl-N'-methylurea
181) N-5-(1-(2-Thienyl)-1-methylethyl)aminocarbonylmethyl-2-methylphenylsulfonyl-N'-methylurea
182) N-5-(1-(3-Thienyl)-1-methylethyl)aminocarbonylmethyl-2-methylphenylsulfonyl-N'-methylurea
183) N-5-(1-(2-Pyrrolyl)-1-methylethyl)aminocarbonylmethyl-2-methylphenylsulfonyl-N'-methylurea
184) N-5-(1-(3-Pyrrolyl)-1-methylethyl)aminocarbonylmethyl-2-methylphenylsulfonyl-N'-methylurea
185) N-5-(1-(2-Thiazolyl)-1-methylethyl)aminocarbonylmethyl-2-methylphenylsulfonyl-N'-methylurea
186) N-5-(1-(3-Thiazolyl)-1-methylethyl)aminocarbonylmethyl-2-methylthiophenylsulfonyl-N'-methylthiourea
188) N-5-(1-(3-Furyl)-1-methylethyl)aminocarbonylmethyl-2-methylthiophenylsulfonyl-N'-methylthiourea
189) N-5-(1-(2-Thienyl)-1-methylethyl)aminocarbonylmethyl-2-methylthiophenylsulfonyl-N'-methylthiourea
190) N-5-(1-(3-Thienyl)-1-methylethyl)aminocarbonylmethyl-2-methylthiophenylsulfonyl-N'-methylthiourea
191) N-5-(1-(2-Pyrrolyl)-1-methylethyl)aminocarbonylmethyl-2-methylthiophenylsulfonyl-N'-methylthiourea
192) N-5-(1-(3-Pyrrolyl)-1-methylethyl)aminocarbonylmethyl-2-methylthiophenylsulfonyl-N'-methylthiourea
193) N-5-(1-(2-Thiazolyl)-1-methylethyl)aminocarbonylmethyl-2-methylthiophenylsulfonyl-N'-methylthiourea
194) N-5-(1-(3-Thiazolyl)-1-methylethyl)aminocarbonylmethyl-2-methylthiophenylsulfonyl-N'-methylthiourea
195) N-5-(1-(2-Furyl)-1-methylethyl)aminocarbonylmethyl-2-methylthiophenylsulfonyl-N'-methylurea
196) N-5-(1-(3-Furyl)-1-methylethyl)aminocarbonylmethyl-2-methylthiophenylsulfonyl-N'-methylurea
197) N-5-(1-(2-Thienyl)-1-methylethyl)aminocarbonylmethyl-2-methylthiophenylsulfonyl-N'-methylurea
198) N-5-(1-(3-Thienyl)-1-methylethyl)aminocarbonylmethyl-2-methylthiophenylsulfonyl-N'-methylurea
199) N-5-(1-(2-Pyrrolyl)-1-methylethyl)aminocarbonylmethyl-2-methylthiophenylsulfonyl-N'-methylurea
200) N-5-(1-(3-Pyrrolyl)-1-methylethyl)aminocarbonylmethyl-2-methylthiophenylsulfonyl-N'-methylurea
201) N-5-(1-(2-Thiazolyl)-1-methylethyl)aminocarbonylmethyl-2-methylthiophenylsulfonyl-N'-methylurea
202) N-5-(1-(2-Furyl)-1-methylethyl)aminocarbonylmethyl-2-ethoxyphenylsulfonyl-N'-methylthiourea
203) N-5-(1-(3-Furyl)-1-methylethyl)aminocarbonylmethyl-2-ethoxyphenylsulfonyl-N'-methylthiourea
204) N-5-(1-(2-Thienyl)-1-methylethyl)aminocarbonylmethyl-2-ethoxyphenylsulfonyl-N'-methylthiourea
205) N-5-(1-(3-Thienyl)-1-methylethyl)aminocarbonylmethyl-2-ethoxyphenylsulfonyl-N'-methylthiourea
206) N-5-(1-(2-Pyrrolyl)-1-methylethyl)aminocarbonylmethyl-2-ethoxyphenylsulfonyl-N'-methylthiourea
207) N-5-(1-(3-Pyrrolyl)-1-methylethyl)aminocarbonylmethyl-2-ethoxyphenylsulfonyl-N'-methylthiourea
208) N-5-(1-(2-Thiazolyl)-1-methylethyl)aminocarbonylmethyl-2-ethoxyphenylsulfonyl-N'-methylthiourea
209) N-5-(1-(3-Thiazolyl)-1-methylethyl)aminocarbonylmethyl-2-ethoxyphenylsulfonyl-N'-methylthiourea
210) N-5-(1-(2-Furyl)-1-methylethyl)aminocarbonylmethyl-2-ethoxyphenylsulfonyl-N'-methylurea
211) N-5-(1-(3-Furyl)-1-methylethyl)aminocarbonylmethyl-2-ethoxyphenylsulfonyl-N'-methylurea
212) N-5-(1-(2-Thienyl)-1-methylethyl)aminocarbonylmethyl-2-ethoxyphenylsulfonyl-N'-methylurea
213) N-5-(1-(3-Thienyl)-1-methylethyl)aminocarbonylmethyl-2-ethoxyphenylsulfonyl-N'-methylurea
214) N-5-(1-(2-Pyrrolyl)-1-methylethyl)aminocarbonylmethyl-2-ethoxyphenylsulfonyl-N'-methylurea
215) N-5-(1-(3-Pyrrolyl)-1-methylethyl)aminocarbonylmethyl-2-ethoxyphenylsulfonyl-N'-methylurea
216) N-5-(1-(2-Thiazolyl)-1-methylethyl)aminocarbonylmethyl-2-ethoxyphenylsulfonyl-N'-methylurea
217) N-5-(1-(2-Furyl)-1-methylethyl)aminocarbonylmethyl-2-propoxyphenylsulfonyl-N'-methylthiourea
218) N-5-(1-(3-Furyl)-1-methylethyl)aminocarbonylmethyl-2-propoxyphenylsulfonyl-N'-methylthiourea
219) N-5-(1-(2-Thienyl)-1-methylethyl)aminocarbonylmethyl-2-propoxyphenylsulfonyl-N'-methylthiourea
220) N-5-(1-(3-Thienyl)-1-methylethyl)aminocarbonylmethyl-2-propoxyphenylsulfonyl-N'-methylthiourea
221) N-5-(1-(2-Pyrrolyl)-1-methylethyl)aminocarbonylmethyl-2-propoxyphenylsulfonyl-N'-methylthiourea
222) N-5-(1-(3-Pyrrolyl)-1-methylethyl)aminocarbonylmethyl-2-propoxyphenylsulfonyl-N'-methylthiourea 223) N-5-(1-(2-Thiazolyl)-1-methylethyl)aminocarbonylmethyl-2-propoxyphenylsulfonyl-N'-methylthiourea
224) N-5-(1-(3-Thiazolyl)-1-methylethyl)aminocarbonylmethyl-2-propoxyphenylsulfonyl-N'-methylthiourea
225) N-5-(1-(2-Furyl)-1-methylethyl)aminocarbonylmethyl-2-propoxyphenylsulfonyl-N'-methylurea
226) N-5-(1-(3-Furyl)-1-methylethyl)aminocarbonylmethyl-2-propoxyphenyl sulfonyl-N'-methylurea
227) N-5-(1-(2-Thienyl)-1-methylethyl)aminocarbonylmethyl-2-propoxyphenylsulfonyl-N'-methylurea
228) N-5-(1-(3-Thienyl)-1-methylethyl)aminocarbonylmethyl-2-propoxyphenylsulfonyl-N'-methylurea
229) N-5-(1-(2-Pyrrolyl)-1-methylethyl)aminocarbonylmethyl-2-propoxyphenylsulfonyl-N'-methylurea
230) N-5-(1-(3-Pyrrolyl)-1-methylethyl)aminocarbonylmethyl-2-propoxyphenylsulfonyl-N'-methylurea
231) N-5-(1-(2-Thiazolyl)-1-methylethyl)aminocarbonylmethyl-2-propoxyphenylsulfonyl-N'-methylurea Preparation of the starting materials
Preparation of 3-sulfamoylphenylalkanecarboxylic acids The 4-substituted phenylalkanecarboxylic acids were added in portions with stirring to an excess of chlorosulfonic acid. The mixture was stirred for 30 minutes at room temperature, then poured onto ice and the resulting sulfonyl chloride was filtered off with suction. The latter was dissolved in ammonia solution, stirred at room temperature for 30 minutes, and the solution was neutralized using 2N hydrochloric acid. The product obtained was filtered off with suction.

Prepared according to this method:
3-Sulfamoyl-4-methoxyphenyl-3-propionic acid M.p. 172°–176° C.
3-Sulfamoyl-4-methoxyphenylacetic acid
M.p. 164° C.

Preparation of 3-sulfonylamino-N-(methylaminothiocarbonyl)-4-methoxyphenylacetic acid 5 g of 3-sulfamoyl-4-methoxyphenylacetic acid were dissolved in 3 ml of DMF and stirred at 40° C. for 30 minutes with 245 mg of sodium hydroxide. 328 mg of methyl isothiocyanate were added thereto and the mixture was stirred for a further 2 h at 70° C. 2N hydrochloric acid was added to the cooled solution and the product was filtered off with suction. M.p. 174° C.

Preparation of N-5-(1-phenylethyl)aminocarbonylmethyl-2-methoxyphenylsulfamoylbenzene 2.45 g (0.01 mol) of 3-sulfamoyl-4-methoxyphenyl-acetic acid and 4.0 g of triethylamine were dissolved in 25 ml of DMF and treated with propanephosphonic anhydride (0.015 mol; 50% strength DMF) and then with 1.2 g (0.01 mol) 1-phenylethylamine with ice cooling. The mixture was stirred for 3 hours at RT and poured onto water. After some time, the product crystallizes and can frequently be used without further purification for further reactions.

The following are obtained analogously
N-5-(1-Phenylethyl)aminocarbonylmethyl-2-ethoxysulfamoylbenzene
N-5-(1-Phenylethyl)aminocarbonylmethyl-2-methylsulfamoylbenzene
N-5-(1-Phenylbutyl)aminocarbonylmethyl-2-ethoxysulfamoylbenzene
M.p.: 156°–158° C.
N-5-(1-Phenylbutyl)aminocarbonylmethyl-2-methylsulfamoylbenzene
M.p.: 117°–118° C.
N-5-(1-Phenylpentyl)aminocarbonylmethyl-2-methoxysulfamoylbenzene
M.p.: 143°–145° C.

General working procedure for the preparation of the sulfonyl(thio)ureas 1 from sulfonamides 2:

A)
0.01 mol of a sulfonamide II were dissolved in 25 ml of DMF and treated with 0.006 mol of $K_2CO_3$. 0.011 mol of an iso(thio)cyanate was added with stirring and the mixture is heated at 60°–80° C. for approximately 2–6 hours. The mixture was poured onto ice water and acidified with 2N HCl. The deposited crystals were filtered off with suction and optionally purified by recrystallization or by chromatography on silica gel. In many cases, however, the reaction was quantitative or the product crystallizes out in pure form after acidifying.

B)
$CS_2$ and KOH in DMF were added to sulfonamide 2, then triphosgene to the dipotassiumsalt. Finally, ammonia was added and the solution was acidified.

EXAMPLES

Example 1

N-5-(1-Phenylethyl)aminocarbonylmethyl-2-methoxyphenylsulfonyl-N'-methylthiourea M.p.: 175°–176° C.

EXAMPLE 2

N-5-(1-Phenylethyl)aminocarbonylmethyl-2-ethoxyphenylsulfonyl-N'-methylthiourea

M.p.: 156°–158° C.

EXAMPLE 3

N-5-(1-Phenylethyl)aminocarbonylmethyl-2-methylphenylsulfonyl-N'-methylthiourea

EXAMPLE 4

N-5-(1-Naphthylethyl)aminocarbonylmethyl-2-methoxyphenylsulfonyl-N'-methylthiourea M.p.: 188°–190° C.

EXAMPLE 5

N-5-(1-Phenylpropyl)aminocarbonylmethyl-2-methoxyphenylsulfonyl-N'-methylthiourea M.p.: 125°–127° C.

EXAMPLE 6

N-5-(1-Phenylbutyl)aminocarbonylmethyl-2-methoxyphenylsulfonyl-N'-methylthiourea M.p.: 128°–130° C.

EXAMPLE 7

N-5-(1-Phenylcyclobutylmethyl)aminocarbonylmethyl-2-methoxyphenylsulfonyl-N'-methylthiourea M.p.: 195°–197° C.

EXAMPLE 8

N-5-(1-Phenylcyclohexylmethyl)aminocarbonylmethyl-2-methoxyphenylsulfonyl-N'-methylthiourea M.p.: 181°–183° C.

EXAMPLE 9

N-5-(1-(2-Methoxyphenyl)ethyl)aminocarbonylmethyl-2-methoxyphenylsulfonyl-N'-methylthiourea M.p.: 178°–179° C.

Example 10

N-5-(1-Phenylpentyl)aminocarbonylmethyl-2-methoxyphenylsulfonyl-N'-methylthiourea M.p.: 143°–145° C.

Example 11

N-5-(1-Phenylpropyl)aminocarbonylmethyl-2-methylsulfonyl-N'-methylthiourea

M.p.: 117°–118° C.

Example 12

N-5-(1-Phenylbutyl)aminocarbonylmethyl-2-methylsulfonyl-N'-methylthiourea

M.p.: 112°–113° C.

EXAMPLE 13

N-5-(1-Phenylcyclobutylmethyl)aminocarbonylmethyl-2-methylphenylsulfonyl-N'-methylthiourea M.p.: 130°–131° C.

EXAMPLE 14

N-5-(1-Phenylcyclohexylmethyl)aminocarbonylmethyl-2-methylphenylsulfonyl-N'-methylthiourea M.p.: 145°–147° C.

EXAMPLE 15

N-5-(2-(1,1R-Phenylethyl)aminocarbonyl)ethyl-2-methoxyphenylsulfonyl-N'-methylthiourea M.p.: 88° C.

EXAMPLE 16

N-5-(2-(1,1S-Phenylethyl)aminocarbonyl)ethyl-2-methoxyphenylsulfonyl-N'-methylthiourea M.p.: 85° C.

EXAMPLE 17

N-5-(2-(1,1R-Phenylethyl)aminocarbonylmethyl-2-methoxyphenylsulfonyl-N'-methylthiourea M.p.: 150°–152° C.

EXAMPLE 18

N-5-(2-(1,1S-Phenylethyl)aminocarbonylmethyl-2-methoxyphenylsulfonyl-N'-methylthiourea M.p.: 150°–152° C.

EXAMPLE 19

N-5-(2-(1,1S-Phenylbutyl)aminocarbonyl)ethyl-2-methoxyphenylsulfonyl-N'-methylthiourea M.p.: 171° C.

Pharmacological data:

The therapeutic properties of the compounds I can be revealed using the following models:

(1) Action potential duration on the papillary muscle of the guinea-pig:

ATP deficiency states, as are observed during ischemia in the cardiac muscle cell, lead to a reduction of the action potential duration. They count as one of the causes of so-called reentry arrhythmias, which can cause sudden heart death. The opening of ATP-sensitive K channels as a result of the fall of ATP counts as causal here.

To measure the action potential, a standard microelectrode technique was employed. For this, guinea-pigs of both sexes were killed by a blow to the head, the hearts were removed, and the papillary muscles were separated out and suspended in an organ bath. The organ bath was irrigated with Ringer solution (0.9% NaCl, 0.048% KCl, 0.024% $CaCl_2$, 0.02% $NaHCO_3$ and 0.1% glucose) and aerated with a mixture of 95% oxygen and 5% carbon dioxide at a temperature of 36° C. The muscle was stimulated by means of an electrode using square-wave impulses of 1 V and i ms duration and a frequency of 2 Hz. The action potential was derived and recorded by means of a glass microelectrode inserted intracellularly, which was filled with 3 mM KCl solution. The substances to be tested were added to the Ringer solution in a concentration of $2.2–10^{-5}$ mol per liter. The action potential is amplified using an amplifier from Hugo Sachs and shown on an oscilloscope. The duration of the action potential was determined at a degree of repolarization of 95% (APD95).

Action potential reductions are produced either by addition of a 1 μM-strength solution of the potassium channel opener Hoe 234 (J. Kaiser, H. Gögelein, Naunyn-Schmiedebergs Arch. Pharm. 1991, 343, R 59) or by addition of 2-deoxyglucose. The action potential-reducing effect of these substances was prevented or reduced by the simultaneous addition of the test substances. Test substances were added to the bath solution as stock solutions in propanediol. The values indicated relate to measurements 30 minutes after addition. Glibenclamide was used in these measurements as a standard. The test concentration in all cases is $2\times10^{10-6}M$.

| Example No. | APD95-start [ms] | APD95-30 min [ms] |
|---|---|---|
| 18 | 179 ± 6 | 140 ± 20 |
| 2 | 173 ± 27 | 152 ± 6 |

We claim:

1. A benzenesulfonylurea or benzenesulfonylthiourea of the formula I

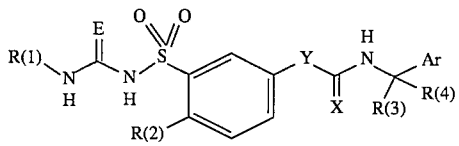

in which:

R(1) is hydrogen, alkyl having 1, 2, 3, 4, 5 or 6 carbon atoms or cycloalkyl having 3, 4, 5 or 6 carbon atoms;

R(2) is alkyl having 1, 2, 3, 4, 5 or 6 carbon atoms, alkoxy having 1, 2, 3, 4, 5 or 6 carbon atoms, mercaptoalkyl having 1, 2, 3, 4, 5 or 6 carbon atoms, cycloalkyl having 3, 4, 5 or 6 carbon atoms or ($C_1$–$C_8$) chains in which one to three carbon atoms can be replaced by O, NH or S;

R(3) and R(4) are identical or different and are hydrogen, alkyl having 1, 2, 3, 4, 5 or 6 carbon atoms, or together form a $(CH_2)_{2-5}$ chain;

E is sulfur;

X is oxygen or sulfur;

is a hydrocarbon chain of the formula $[CR(5)_2]_m$; wherein R(5) is hydrogen or alkyl having 1 or 2 carbon atoms;

m is 1 or 2;

Ar is phenyl, thienyl, furyl, pyrrolyl, thiazolyl, naphthyl, or pyridyl, which in each case is unsubstituted or substituted by one to 3 substituents selected from the group consisting of alkyl having 1 or 2 carbon atoms, alkoxy having 1 or 2 carbon atoms, Cl, Br and F.

2. A compound of the formula I as claimed in claim 1, wherein:

R(1) is hydrogen, alkyl having 1, 2, 3, 4, 5 or 6 carbon atoms or cycloalkyl having 3, 4, 5 or 6 carbon atoms;

R(2) is alkyl having 1, 2, 3, 4, 5 or 6 carbon atoms, alkoxy having 1, 2, 3, 4, 5 or 6 carbon atoms, mercaptoalkyl having 1, 2, 3, 4, 5 or 6 carbon atoms, cycloalkyl having 3, 4, 5 or 6 carbon atoms or ($C_1$–$C_8$) chains in which 1 to 3 carbon atoms can be replaced by O, NH or S;

R(3) and R(4) are identical or different and are hydrogen, alkyl having 1, 2, 3, 4, 5 or 6 carbon atoms or together form a $(CH_2)_{2-5}$ chain;

E is sulfur;

X is oxygen;

Y is a hydrocarbon chain of the formula $[CR(5)_2]_{1-2}$, R(5) is hydrogen or alkyl having 1 or 2 carbon atoms;

Ar is phenyl, thienyl, furyl, pyrrolyl, thiazolyl, naphthyl, or pyridyl, which in each case is unsubstituted or substituted by one to 3 substituents selected from the group consisting of alkyl having 1 or 2 carbon atoms, alkoxy having 1 or 2 carbon atoms, Cl, Br and F.

3. A compound of the formula I as claimed in claim 1, wherein:

R(1) is hydrogen or alkyl having 1 or 2 carbon atoms;

R(2) is alkoxy having 1, 2, 3, 4, 5 or 6 carbon atoms;

R(3) and R(4) are identical or different and are hydrogen, or alkyl having 1, 2, 3, 4, 5 or 6 carbon atoms;

E is sulfur;

X is oxygen;

Y is a hydrocarbon chain of the formula $(CH_2)_{1-2}$;

Ar is phenyl, thienyl, furyl, pyrrolyl, thiazolyl, naphthyl, or pyridyl, which in each case is unsubstituted or substituted by one to 3 substituents selected from the group consisting of alkyl having 1 or 2 carbon atoms, alkoxy having 1 or 2 carbon atoms, Cl, Br and F.

4. A compound of the formula I as claimed in claim 1, wherein:

R(1) is hydrogen or alkyl having 1 or 2 carbon atoms;

R(2) is alkoxy having 1, 2, 3, 4, 5 or 6 carbon atoms;

R(3) and R(4) are identical or different and are hydrogen or methyl;

E is sulfur;

X is oxygen;

Y is a hydrocarbon chain of the formula $(CH_2)_{1-2}$;

Ar is thienyl, furyl, pyrrolyl, thiazolyl, naphthyl, or pyridyl, which in each case is unsubstituted or substituted by one to 3 substituents selected from the group consisting of alkyl having 1 or 2 carbon atoms, alkoxy having 1 or 2 carbon atoms, Cl, Br and F.

5. A compound of the formula I as claimed in claim 1, wherein:

R(1) is hydrogen or alkyl having 1 or 2 carbon atoms;

R(2) is alkoxy having 1, 2, 3, 4, 5 or 6 carbon atoms;

R(3) and R(4) are identical or different and are hydrogen or methyl;

E is sulfur;

X is oxygen;

Y is a hydrocarbon chain of the formula $(CH_2)_{1-2}$;

Ar is phenyl, which is unsubstituted or substituted by one to 3 substituents selected from the group consisting of alkyl having 1 or 2 carbon atoms, alkoxy having 1 or 2 carbon atoms, Cl, Br and F.

6. A pharmaceutical composition comprising an effective amount of a compound of the formula I as claimed in claim 1.

7. A method for the treatment of ischemic conditions of the heart, weakened cardiac power, or cardiac arrhythmias comprising administering an effective amount of the compound of formula I as claimed in claim 1.

8. A method for the prevention of sudden heart death or the improvement of heart function after heart transplantation comprising administering an effective amount of the compound of formula I as claimed in claim 1.

* * * * *

UNITED STATES PATENT AND TRADEMARK OFFICE
CERTIFICATE OF CORRECTION

Page 1 of 2

PATENT NO. : 5,607,976
DATED : March 04, 1997
INVENTOR(S) : Heinrich ENGLERT et al.

It is certified that error appears in the above-indentified patent and that said Letters Patent is hereby corrected as shown below:

Column 4, line 18, in formula V, "$Cl_2C$" should read --$Cl_3C$--;

line 50, " R(1)—N=C=S." should read -- R(1)—N=C=S.         VI--;

line 52, " X=S]" should read-- E=S]--.

Column 15, line 35, "5g of 3-sulfamoyl-4-" should begin a new paragraph;

line 43, "2.45g (0.01 mol)" should begin a new paragraph.

Column 18, line 46, "i ms" should read --1 ms--;

line 67, "$2x10^{10-6}M$" should read --$2x10^{-6}M$--.

UNITED STATES PATENT AND TRADEMARK OFFICE
CERTIFICATE OF CORRECTION

PATENT NO. : 5,607,976
DATED : March 04, 1997
INVENTOR(S) : Heinrich Englert, et. al.

It is certified that error appears in the above-identified patent and that said Letters Patent is hereby corrected as shown below:

Claim 1, column 19, line 31, insert --Y-- before "is".

Signed and Sealed this

Thirtieth Day of June, 1998

BRUCE LEHMAN

*Commissioner of Patents and Trademarks*